(12) United States Patent
Doyle

(10) Patent No.: US 6,390,998 B1
(45) Date of Patent: May 21, 2002

(54) HINGE MECHANISM FOR A LIMB PROTECTOR

(76) Inventor: Kelvin Doyle, 4 Artillery Pl., Mepham Crescent, Harrow, Middx (GB), HA3-6Q2

( * ) Notice: Subject to any disclaimer, the term of this patent is extended or adjusted under 35 U.S.C. 154(b) by 0 days.

(21) Appl. No.: 09/380,340

(22) PCT Filed: Mar. 5, 1998

(86) PCT No.: PCT/GB98/00713

§ 371 Date: Nov. 29, 1999

§ 102(e) Date: Nov. 29, 1999

(87) PCT Pub. No.: WO98/38964

PCT Pub. Date: Sep. 11, 1998

(30) Foreign Application Priority Data

Mar. 5, 1997 (GB) .............................................. 9704586

(51) Int. Cl.$^7$ ................................................. A61F 5/00
(52) U.S. Cl. ......................................... 602/26; 602/16
(58) Field of Search ............................... 602/5, 16, 26, 602/23, 27, 20, 21; 128/882, 878–879; 16/366, 357; 623/39

(56) References Cited

U.S. PATENT DOCUMENTS

| | | | | | |
|---|---|---|---|---|---|
| 2,632,440 | A | * | 3/1953 | Hauser | 602/16 |
| 4,802,467 | A | * | 2/1989 | Pansiera | 602/16 |
| 4,886,054 | A | * | 12/1989 | Castillo | 602/26 |
| 5,009,223 | A | * | 4/1991 | DeFonce | 602/16 |
| RE33,621 | E | * | 6/1991 | Lamb | 602/16 |
| 5,107,824 | A | * | 4/1992 | Rogers et al. | 602/16 |
| 5,168,865 | A | * | 12/1992 | Radcliffe | 602/16 |
| 5,490,822 | A | * | 2/1996 | Biedermann | 602/16 |

* cited by examiner

Primary Examiner—Denise Pothier

(57) ABSTRACT

A brace or limb protector, which in hinging, matches the complex bending motion of the natural knee of a human being. The hinge mechanism has supports for the upper and lower leg which are attached to each other by a hinging mechanism which is connected to and pivots on the support at a first position (50) and a second position (72) respectively. Connection of the supports at the first position (50) is to the plate of the hinge mechanism and at the second position (72) to the arm which pivots on the plate at stud (61). This configuration of the hinging system allows the hinge mechanism of the brace or limb protector to follow the natural movements of the human knee at all degrees of natural movement.

6 Claims, 2 Drawing Sheets

HINGE MECHANISM FOR A LIMB PROTECTOR

RELATED APPLICATION

The priority claim is of Pat. No. PCT/GB98/00713, filing date Mar. 5, 1998, Priority date Mar. 5, 1997

This invention relates to a hinge mechanism for a limb protector for the joint of a human limb, that is a knee or elbow protector. Therefore it can have related application as a knee or elbow brace.

BACKGROUND TO THE INVENTION

Injuries to the limbs and their joints occur for several reasons, including participation in contact sports such as American football ice hockey, in individual sports such as skiing or motorcycle racing or indeed any active sport. In addition injuries to limbs and their joints occur in active occupations such as armed forces, or in any type of accident.

After an injury occurs, it is often desirable to either slightly restrict the movement of the limb or the joint, for example by elastic support, or severely restrict movement of the limb or joint by ridged splits, or ridged braces that restrict the degree of movement of the limb or joint, for example by hinged knee or elbow braces, (de-rotational braces).

Such braces which are available to prevent twisting of a knee or elbow can be worn during activities such as skiing and can have preventative as well as protective effect. Such hinged braces are by their very nature restrictive of movement and permit only forward bending of the knee or elbow. Other braces are available for sports such as American football which protects the knee against side impact or frontal impact but also restrict movement (prophylactic or preventative braces). Dynamic braces are also available with eccentrically placed hinges to provide protection to torn ligaments. The present invention relates to rigid hinged braces.

RELATED ART

WO 94/18916 discloses a variety of hinged braces to be worn for the protection or support of a damaged or potentially damageable joint. The braces disclosed have, when applied to a knee joint, respective upper and lower rigid supports which engage the leg above and below the knee and which are hinged one to the other to allow bending of the joint.

Because of the way the joint of the human knee is physically constructed the bending of a joint can occur around any point within a given area covering that joint when that joint is viewed from the side, or in a direction substantially parallel to the axis of rotation of the exact point about which the joint rotates is dependent upon the the limb either side of the joint, or the amount by which the limb, and hence the joint has already been bent. When for example the joint being rotated is the knee, the points about which rotation may occur may be either side of the cartilage that separates the tibia and fibula bones on the one side, and the femur on the other side of the knee joint or on both sides of the cartilage. Accordingly, to hinge the upper and lower supports together about a simple pivot is unsatisfactory. Instead, in preferred constructions as shown in FIGS. 5 and 16 of WO 94/18916, each is pivoted to an intermediate member and the two intermediate members are pivoted to one another. This allows the axis of rotation to vary relative to the joints, e.g. When moving from standing vertically to bending one's knees. The assembly shown in WO94/18916 are cumbersome and complex to assemble, and require the manufacture of a plurality of telescopic shells which must slide over one another easily, but which must be sufficiently rigid and impact resistant (as such braces are often worn during contact sport play to enable play to occur but reducing the risk of further injury to a recovering limb) to ensure that such movement can be maintained without jamming. These criteria are not easy to meet.

I have now found that a much more effective and robust hinging mechanism can be provided which maintains the flexibility of movement provided by the constructions shown in WO 94/18916, but which does not incur its disadvantages. In particular, it may enable easy assembly and disassembly and is very resistant to mechanical damage.

BRITISH GOVERNMENT SPONSORED RESEARCH GRANT

The development of this invention was funded by the United Kingdom Grant: Supports for Products Under Research grant, this grant was known as the SPUR grant.

BRIEF SUMMARY OF THE INVENTION

According to the present invention there is provided a hinge mechanism for a limb protector including first and second supports each adapted to engage a part of a limb in either side of an articulated joint, the hinge mechanism being pivotally connected to both supports, and wherein the hinge mechanism comprises a base plate, an arm pivotally rotatable against the plate about an axis substantially perpendicular thereto and located to one end of the arm and means (by way of connecting screws) for connecting the support members pivotally to the other end of the arm and to the plate, all of these three axes of rotation of the pivotal connections being substantially parallel, and wherein associated with each of the three pivotal connections are means for restricting the relative degree of rotation of the respective two members to a defined amount.

Preferably, the arm is mounted rotationally on a circular boss on the plate and the plate has stop means formed thereon restricting the angular rotation of the arm, e.g. to a maximum of 60 degrees. Preferably, the angular rotation of each support member relative to the end of the arm or the base plate respectively is restricted by the passage of a stud or post along an arcuate slot centred on the pivot axis.

The post is conveniently on the base or arm and the arcuate slot in the support member. The extent of the arcuate slot may vary, but is commonly in the range of 50 degrees to 110 degrees.

By hinging of the supports together using a hinge mechanism according to the present invention, with all three pivots having a restricted degree of rotation, the degree of rotation of each of the first, second and third pivotal connections may be set to predetermine the maximum translational and rotational movement between the bones of the joint around which the brace is to be fixed. This may be achieved by providing slots of lengths corresponding to the maximum likely desired degree of pivotal movement, e.g. 60 and 90 degrees and then limiting the degree of rotation of either or both slots by inserting into the arcuate slot spacers or other means of preventing rotation, so that the relevant studs or posts may move only along a portion of that slot.

The degree of rotation available to the arm may be limited by locating the arm in a recessed portion of the plate which is bounded by radial walls e.g. inclined at 60 degree to one another. To limit the degree of rotation further spacers or other means of preventing rotation may be fixed within the recess. In place of a recess with walls, the amount of rotation of the arm may be defined by studs mounted on the plate. The hinge mechanism of the present invention may be made of any suitable material, preferably aluminium alloy, though, if desired, suitable engineering plastics materials may be used. The support members are conventionally made of rigid material. In order to avoid over stressing such materials where they are connected to the hinge mechanism, reinforcements, e.g. of metal, may be installed. In particular, it is found useful to reinforce the edges of the arcuate slots with a metal plate or liner.

In use, each limb protector or brace would have a hinge mechanism according to the present invention on either side of the joint around which the brace was placed.

The hinge of the present invention may be employed on all currently known types of kneebrace once suitable modification has been made to those knee braces. In particular, the present invention is of value applied to braces as described in WO 94/18916, with the arrangement as described above replacing the front plates of the hinged brace described therein.

BRIEF DESCRIPTION OF THE DRAWING

The invention is illustrated by way of example with reference to the accompanying drawings in which.

DETAILED DESCRIPTION OF INVENTION

Figure 1:
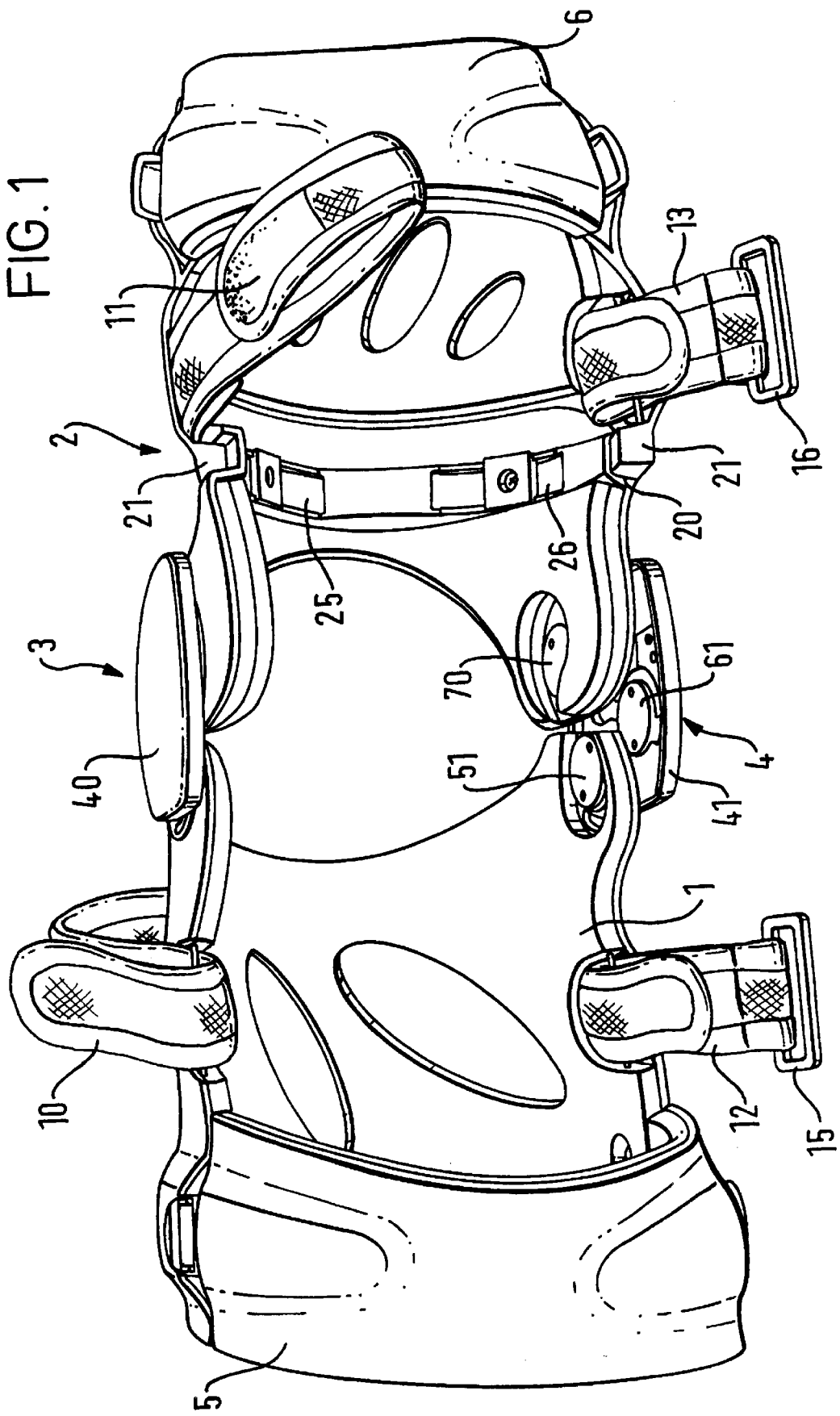
FIG. 1 shows a perspective view of the knee brace incorporating a hinge mechanism according to the present invention.

Referring to FIG. 1, the knee brace which is illustrated lying on its side and from the back as shown in the drawings, consist basically of upper and lower hollow shell or supports members 1 and 2 are respectively shaped to accommodate the thigh and calf of the wearer. Members 1 and 2 are joined by hinge mechanism 3 and 4, described in more detail below, and may be held on the respective parts of the legs by means of hard moulded semi-cylindrical portions 5 and 6. Projecting from the ends of portions 5 and 6 are locating tabs and straps which fit into corresponding apertures in members 1 and 2 via appropriate snap action catches enabling each to be pushed towards the member 1 and 2 respectively to fit snugly around the thigh or calf respectively. Substantially the whole of the interior of members 1 and 2, 5 and 6 is lined with a cushioning foam for comfort. Fitted to the interior of each of the members 1 and 2 are some short metal rods which are substantially vertical when the brace is worn with the wearer standing upright. These are obscured in the drawing by double-sided burr fastener straps 10, 11, 12 and 13. Straps 12 and 13 are relatively short and one end of each terminates in an elongate plastics ring 15 and 16 respectively through which the free end of the rather longer straps 10 and 11 may be passed and then folded back on itself to tension each strap round the rear of the lower thigh and upper calf respectively. The central portions of the longer strap 10 and 11 may be fabrics faced than faced with burr fastener material, for greater comfort. Hollow shell member 2 is constructed in two parts, the left hand one of which as shown in the drawing has an annular outward facing groove 20 and the other portion of which to the right in FIG. 1 has an annular inward facing rib 21. Rib 21 can slide in the annular grove to a certain extent, thus allowing a limited degree of swivelling between the portion of the brace which is attached to the thigh and the portion which is attached to the calf. This swivel feature is described in more detail in Specification WO94/18916. The right hand portion of member 2 is held captive in the left hand portion by means of a pair of squat T-section bosses which pass through two short slots 25 and 26 located in the base of groove 20.

In accordance with the invention, members 1 and 2 are held together by two hinged mechanisms 3 and 4. Each of hinge mechanism 3 and 4 consists of a base plate 40, 41 respectively which is pivotally attached directly to member 1 and which has mounted on it a swivellable arm to the free end of which is pivotally attached member 2.

Figure 2:
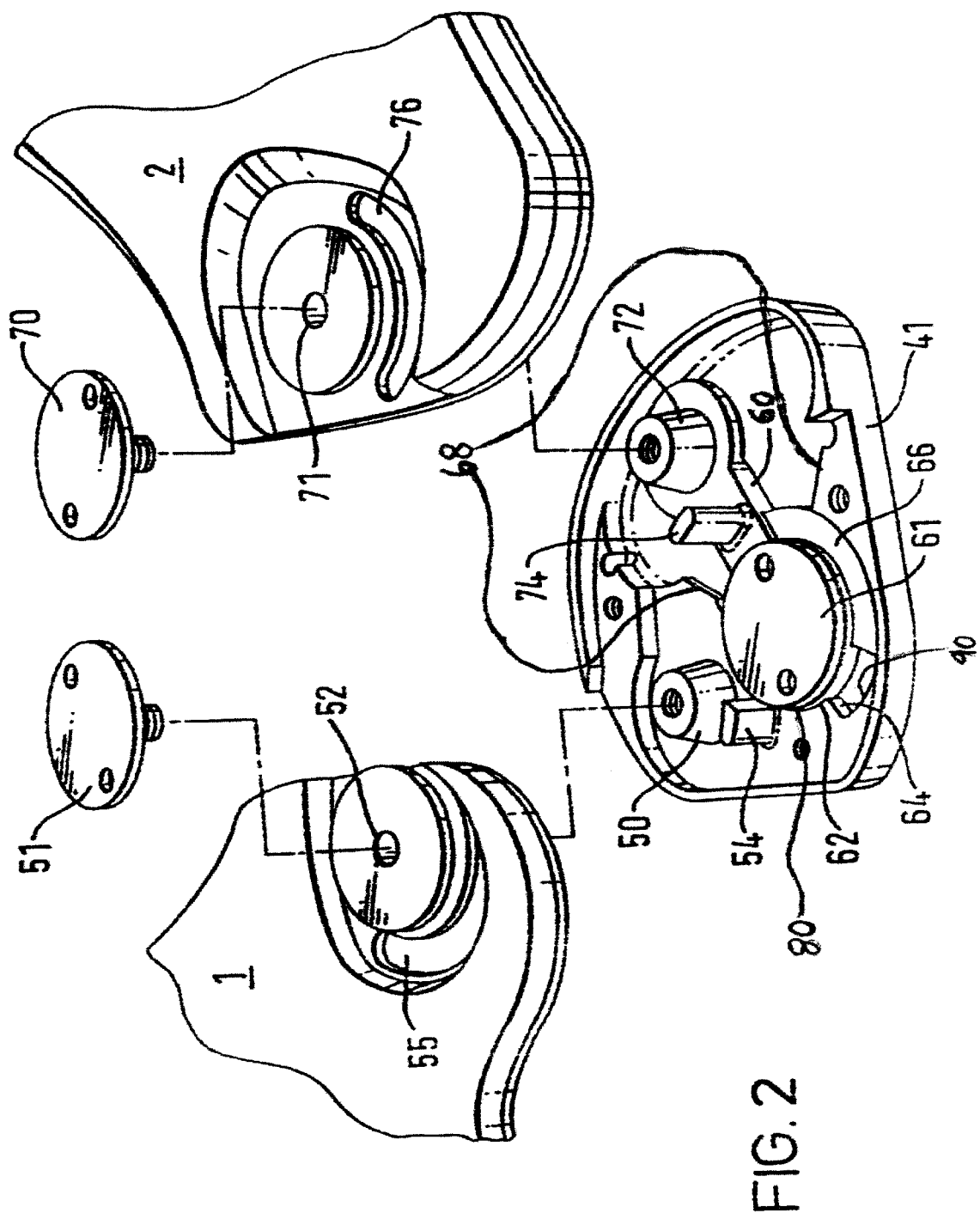
FIG. 2 shows a detail of the brace of FIG. 1 in exploded view.

The detailed construction of the hinge mechanism 4 is shown in FIG. 2. The construction of hinge mechanism 3 is identical save for being a mirror image of hinge mechanism 4. Referring now to FIG. 2, this shows an exploded view of the hinge mechanism with the two members 1 and 2 detached from the base plate 41 and the arm contained therein, for clarity of explanation.

Base plate 41 has two threaded bosses on its surface facing hinge mechanism 3. One of these, denoted 50 in FIG. 2, acts as the pivotal connection between base plate 41 and member 1 and pivots about an axis substantially perpendicular to the base plate 41. For this purpose, a lockable threaded stud 51 may be passed through an aperture 52 in member 1 and screwed into boss 50 which is internally threaded.

As that occurs, an upstanding arcuate tab 54 enters in to an arcuate slot 55 in the material of members 1, slot 55 being centred on aperture 52. Not shown in the drawing is a metal reinforcement which is moulded into the exterior of member 1 and which has an aperture registered with aperture 52 and arcuate slot registered with arcuate slot 55. When member 1 is accordingly assembled on to base plate 41, it can pivot relative thereto, but only to the extent allowed by the travel of tab 54 in slot 55.

If it is desired to restrict the range of rotation of member 1 relative to base plate 41, a suitable stop member may be inserted at one or both ends of slot 55.

Mounted on base plate 41 is a swivel arm 60. The left hand of this arm as seen in FIG. 2 is of ring shape and fitted round a further threaded post formed integrally with base plate 41 and held in place by a screw-in stud 61. The circular left hand end of arm 60 is located in a generally circular recess 62 in the base the plate 41. This recess is a continuation of the internal wall 68 and is formed from two radial sections, one 80 having a radius only slightly greater than the radius of the ring on the left hand arm of arm 60 and the other 90 having an enlarged radius forming the two part cylindrical wall of recess 62 abutting at a shoulder 64 which lies in a radial plane relative to the hidden threaded stud about which arm 60 may swivel. On one side of the generally ring-shaped end of arm 60 is a partial annular flange 66 which, when its end as shown on the left in FIG. 2 abuts shoulders 64, limits the clockwise rotation of arm 60. The anti-clockwise rotation is limited by the right hand end of arm 60 as shown in FIG. 2 coming to abut an internal wall 68 formed in base member 41. Thus, arm 60 may swivel through a defined angle, which may be reduced by inserting packing members against shoulder 64 or wall 68 if it is desired to do so. It can be also be seen that the radial sections 80, 90 which are part of wall 68 are lined at an angle to one another.

Member 2 is pivotally connected to the right hand end of arm 60 about an axis substantially perpendicular to the base plate by means of a threaded stud 70 which passes through an aperture 71 in member 2 and into a threaded post 72 on the end of arm 60. Arm 60 is formed with an upstanding tab 74 or post which, when member 2 is assembled on to the arm 60, passes through an arcuate slot 76 in member 2.

Again, the extent of rotation permitted between arm 60 and member 2 may be reduced by inserting stop members into one or both ends of arcuate slot 76.

The outer periphery of base plate 41 may be contoured so that its inner face lies closely against the exterior faces of members 1 and 2 thus reducing the ingress of dirt or other contamination when the knee brace is worn. The hinge mechanism 3 and 4 permit natural flexure of the wearer's leg with the three pivotal connections, the pivot axes of which correspond to the threaded shafts of studs 51, 61 and 70, enabling a natural and comfortable movement to occur. Excessive flexure of the joint, beyond what the wearer's medical or physiotherapist advisors would recommend, may be prevented by restricting the range of angular movement of one, two or all three of these pivotal connections by the use of packing members as indicated above. The support members are made from rigid plastic or fibre reinforced resin type composition.

I claim:

1. A knee brace including:
   (a) a first and second support members, the first and second support members adapted to engage a leg on either side of a knee joint; and
   (b) a hinge mechanism comprising:
      (i) a base plate having a recessed portion bounded by radial walls and
      (ii) a swivel arm having a first and second end, the first end of the arm located in the recessed portion, wherein the first support member pivotally connects to the base plate, the first end of the arm pivotally rotates against the plate about an axis substantially perpendicular thereto in the recessed portion and a means for pivotally connecting to the second end of the arm to the second support member about an axis substantially perpendicular to the base plate and further wherein the second support member has an arcuate slot and the arm has a post for engaging the arcuate slot to limit pivotal movement of the second support member with respect to the arm, such that the swivel arm, the post, the arcuate slot and the radial walls restrict the degree of angular rotation of the first and second support members.

2. A knee brace according to claim 1, wherein the swivel arm is mounted rotationally on a circular boss on the base plate and the first support member has a stop member formed thereon restricting the movement of the arm.

3. A knee brace according to claim 1, wherein a tab is on the base plate and a second arcuate slot is in the first support member.

4. A knee brace according to claim 3, wherein the angular rotation of the first and second support members is restricted by the passage of the post along the arcuate slot and the tab along the second arcuate slot.

5. A knee brace according to claim 4, further including at least one spacer inserted into the arcuate slot or the second arcuate to limit the degree of rotation.

6. A knee brace according to claim 1, wherein the first and second support members are made of rigid reinforced material.

* * * * *